(12) United States Patent
Butler et al.

(10) Patent No.: US 9,586,009 B2
(45) Date of Patent: Mar. 7, 2017

(54) DRUG DELIVERY DEVICE

(75) Inventors: Joseph Butler, Warwickshire (GB); David Moore, Leicestershire (GB); Paul Richard Draper, Worcestershire (GB); Stephen Francis Gilmore, Bristol (GB); Anthony Paul Morris, Coventry (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 484 days.

(21) Appl. No.: 14/131,646

(22) PCT Filed: Jul. 12, 2012

(86) PCT No.: PCT/EP2012/063627
§ 371 (c)(1),
(2), (4) Date: Jan. 8, 2014

(87) PCT Pub. No.: WO2013/010889
PCT Pub. Date: Jan. 24, 2013

(65) Prior Publication Data
US 2014/0171879 A1    Jun. 19, 2014

Related U.S. Application Data

(60) Provisional application No. 61/570,307, filed on Dec. 14, 2011.

(30) Foreign Application Priority Data

Jul. 15, 2011   (EP) ..................................... 11174124

(51) Int. Cl.
*A61M 5/315*   (2006.01)
*G01D 5/249*   (2006.01)
(Continued)

(52) U.S. Cl.
CPC .... *A61M 5/31585* (2013.01); *A61M 5/31525* (2013.01); *A61M 5/31551* (2013.01);
(Continued)

(58) Field of Classification Search
CPC ...... A61M 5/31551; A61M 2005/2488; A61M 2005/3126; A61M 2205/52;
(Continued)

(56) References Cited

U.S. PATENT DOCUMENTS 5,662,612 A * 9/1997 Niehoff ............. A61M 5/14546
417/15
2004/0210199 A1 * 10/2004 Atterbury ......... A61M 5/31566
604/224

(Continued)

FOREIGN PATENT DOCUMENTS

| WO | 2006045523 A1 | 5/2006 |
|----|---------------|--------|
| WO | 2007116090 A1 | 10/2007 |
| WO | 2010052275 A2 | 5/2010 |
| WO | 2010098927 A1 | 9/2010 |
| WO | 2010139640 A1 | 12/2010 |

*Primary Examiner* — Nathan R Price
*Assistant Examiner* — Gerald Landry, II
(74) *Attorney, Agent, or Firm* — McDonnell Boehnen Hulbert & Berghoff LLP

(57) ABSTRACT

A drug delivery device comprising; a housing; a cylindrical member configured to be rotatably supported inside the housing, wherein the outer surface of the cylindrical member is provided with at least first and second tracks together forming an encoder, each track comprising conductive segments and non-conductive segments; and at least first and second groups of contacts configured to engage the first and second tracks respectively at predetermined intervals along the length of the track.

15 Claims, 10 Drawing Sheets

(51) Int. Cl.
*G01D 5/25* (2006.01)
*A61M 5/24* (2006.01)
*A61M 5/31* (2006.01)

(52) U.S. Cl.
CPC ....... *A61M 5/31593* (2013.01); *G01D 5/2497* (2013.01); *G01D 5/25* (2013.01); *A61M 5/31541* (2013.01); *A61M 2005/2488* (2013.01); *A61M 2005/3125* (2013.01); *A61M 2005/3126* (2013.01); *A61M 2205/52* (2013.01)

(58) Field of Classification Search
CPC ...... A61M 2005/3125; A61M 5/31593; A61M 5/31525; A61M 2205/3306; A61M 2205/6072; G01D 5/2497; G01D 5/1655
USPC ........................................ 604/189, 207, 224
See application file for complete search history.

(56) References Cited

U.S. PATENT DOCUMENTS

| | | | |
|---|---|---|---|
| 2006/0118612 A1* | 6/2006 | Christoffersen | A61J 1/06 235/375 |
| 2007/0123829 A1* | 5/2007 | Atterbury | A61M 5/31566 604/207 |
| 2009/0088701 A1* | 4/2009 | Larsen | A61M 5/24 604/189 |
| 2010/0106098 A1* | 4/2010 | Atterbury | A61M 5/31566 604/207 |
| 2011/0270214 A1* | 11/2011 | Jorgensen | A61M 5/31551 604/500 |
| 2011/0313349 A1* | 12/2011 | Krulevitch | A61M 5/24 604/65 |

* cited by examiner

DRUG DELIVERY DEVICE

CROSS REFERENCE TO RELATED APPLICATIONS

The present application is a U.S. National Phase Application pursuant to 35 U.S.C. §371 of International Application No. PCT/EP2012/063627 filed Jul. 12, 2012, which claims priority to European Patent Application No. 11174124.5 filed Jul. 15, 2011 and U.S. Provisional Patent Application No. 61/570,307 filed Dec. 14, 2011. The entire disclosure contents of these applications are herewith incorporated by reference into the present application.

FIELD OF INVENTION

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

A first aspect of the invention provides a drug delivery device comprising;
 a housing;
 a cylindrical member configured to be rotatably supported inside the housing, wherein the outer surface of the cylindrical member is provided with at least first and second tracks together forming an encoder, each track comprising conductive segments and non-conductive segments; and
 at least first and second groups of contacts configured to engage the first and second tracks respectively at predetermined intervals along the length of the track.

The encoder is formed at least of first and second tracks wherein the coding depth of the at least two tracks is combined. Describing the coding depth in numbers of bits, the combined bit depth of the encoder comprising the at least first and second track equals the sum of the individual bit depth of each track. For example, the encoder could have a 7-bit depth comprising a 5-bit depth first track and a 2-bit depth second track. Alternatively, the individual tracks comprise 4-bit and 3-bit depths, respectively, together forming an encoder of 7-bit depth. A 7-bit code that is capable of encoding $2^7$ different states is sufficient to encode the positions of an 80 unit medicament pen-type drug delivery device.

The encoder may be adapted to capture a dose that has been set.

The tracks may comprise conductive ink printed onto a non-conductive substrate

The first and second tracks may be separated. The first and second tracks may be separated by a non-conductive strip. The non-conductive strip may be the cylindrical member itself or a secondary substrate which is subsequently attached to the cylindrical member.

The cylindrical member may be operationally coupled to the dose setting and delivery mechanism, for example by securing the cylindrical member to a dose dial grip and by having a rotatable engagement between the cylindrical member and an inner housing that is connected to a spindle that is driven during dose administration.

The tracks may be helical tracks and the housing and the cylindrical member may be configured such that the cylindrical member moves in a first axial direction relative to the housing when rotated in a first rotational direction relative to the housing.

The cylindrical member may be configured to be rotatable from an initial position into a number of discrete rotational positions and the contacts of the first group of contacts may be arranged such that the sequence of conductive and non-conductive segments engaged by the contacts of the first group of contacts in successive discrete rotational positions forms a Gray code.

The first group of contacts may comprise more contacts than the second group of contacts. The first group of contacts may comprise five contacts and the second group of contacts may comprise two contacts.

The contacts of the first group of contacts may be spaced such as to engage every sixth segment of the first track and the contacts of the second group of contacts may be spaced such as to engage every twenty-seventh segment of the second track.

The device may further comprise a switch configured:
 in a first position, to connect electrically the first and second tracks; and
 in a second position, to isolate electrically the first and second tracks.

The device may further comprise a user actuatable plunger configured to cause expulsion of a drug from the drug delivery device wherein depression of the plunger may cause the switch to switch from the first position to the second position.

The conductive segments within each of the first and second tracks may be electrically connected to all of the other conductive segments in that track. The conductive segments within each of the first and second tracks may be electrically connected together by first and second common ground tracks immediately adjacent to respective ones of the first and second tracks. The conductive and non-conductive segments of the first and second tracks may be arranged such that, when the cylindrical member is in an initial position, each contact is configured to engage a conductive segment.

The device may further comprise;
 a display; and
 a processor configured to receive and interpret electrical signals from the contacts, to control application of electrical signals to the contacts and to control the operation of the display.

The processor may be configured to cause an electrical signal to be applied to at least a first contact of the second group of contacts and simultaneously to monitor signals at at least one other contact in order to determine a position of the cylindrical member. Based at least in part on the monitored signals, the processor may be configured to determine the position of the encoded member. The processor may further be configured to determine the mode of operation.

The processor may be configured:

to cause an electrical signal to be applied to a first contact of the second group of contacts and simultaneously to monitor electrical signals at the first group of contacts; and if no signals are detected at any of the first group of contacts, to cause an electrical signal to be applied to a second contact of the second group of contacts and simultaneously to monitor electrical signals at the first group of contacts.

The processor may be responsive to detecting no signals at any of the first group of contacts when an electrical signal is applied to the second contact of the second group of contacts to cause an electrical signal to be applied to a first contact of the first group of contacts and simultaneously to monitor electrical signals at the other contacts of the first group of contacts.

Another aspect of the invention relates to combining of at least two smaller bit depth single track encoders to create a higher bit depth encoder.

A standard 7-bit track encoder, e.g., comprises 7 tracks arranged in parallel that require a relatively wide area on an encoded member. Having, for example, the encoder track on a rotating sleeve, a helical version of the encoder would need to fit in the axial pitch, i.e. the space between two windings. According to our example, the 7 parallel tracks would have to fit the space between two windings for a given pitch, wherein the width of each track is very limited. This puts constraints with regards to the individual track width, and construction complexity increases. Fitting 7 parallel tracks in the restricted space results in a high requirement for the read-out accuracy of the encoder with regards to both, the coded tracks as well as the sensors. The length of the tracks depends on the number of positions that are requested to be encoded, e.g. 81 positions for an 80 unit pen, including a zero position.

An alternative 7-bit single track encoder, e.g., could be adapted to require a width smaller than the standard 7-bit track encoder described before. Instead of having the tracks in parallel, a single track is used where the sensors representing the bits are equally spaced along this track. For an encoder track on a rotating sleeve, a single track could more easily to fit in the axial pitch, i.e. the space between two windings. The encoder may be constructed using a single track gray code, where each column is a cyclic shift of the first column (according to the number of sensors) and from any row to the next row only one bit changes. The spacing of the sensors may be 12, e.g., i.e. a sensor is positioned every $12^{th}$ position. When the first sensor is at position "1" the seventh sensor is at position "72". Having, for example, the encoder track on a rotating sleeve, a helical version of the encoder would require adding the pattern of the single track to the end, because otherwise, the sensors would have no track to read. This means that an extra 72 positions are required to make sure that the seventh sensor or bit 7 maintains engagement with the track. Therefore the solution for a 7-bit single track encoded is 81+72=153 units long compared with 81 units long for the standard 7 track version discussed before. The effect of having a track of relatively small width results in extended total length of the track, compared to the standard 7-bit encoder. A rotating sleeve carrying a single track encoder would consequently have an increased axial size. This could add complexity to the design of the device and eventually could lead to an extended overall delivery device length.

The above mentioned principles apply to encoders regardless of the number of bits for the encoder track.

An encoder according to the invention, wherein the at least first and second tracks together forming an encoder, could help mitigating the deficiencies of the two types of encoders mentioned above. An encoder according to the invention requires a width smaller compared to a standard "parallel-track" encoder. The encoder according to the invention requires a length shorter compared to a "single track" encoder. Thus the encoder according to the present invention provides an improved encoder that may increase manufacturing quality, reduce cost, and/or increase code efficiency.

The encoder according to the present invention comprises at least two single track bit-codes, e.g. single track gray codes, together forming an encoder, wherein the encoder has a higher bit depth than each individual track.

In one example, a combination of a 5-bit track and a 2-bit track together form an encoder of 7-bit depth. The 5-bit track may have a spacing of 6, therefore the 5th sensor or contact is at position 24. The overall track length required for a helical version is 81+24=105. The 2-bit track may have a spacing of 27, therefore the helical track length is 81+27=108.

The combined encoder having a 7-bit depth comprises two tracks and has a length of 108. Compared to a single track 7-bit code, the length is reduced by approximately ⅓ (compared 153) which reduces the overall size of the encoded member. Compared to a standard 7-bit track, the width is reduced from "7" to "2" which leaves more space for each individual track.

BRIEF DESCRIPTION OF THE DRAWINGS

Embodiments will now be described, by way of example only, with reference to the accompanying drawings, in which.

DETAILED DESCRIPTION

Figure 1:
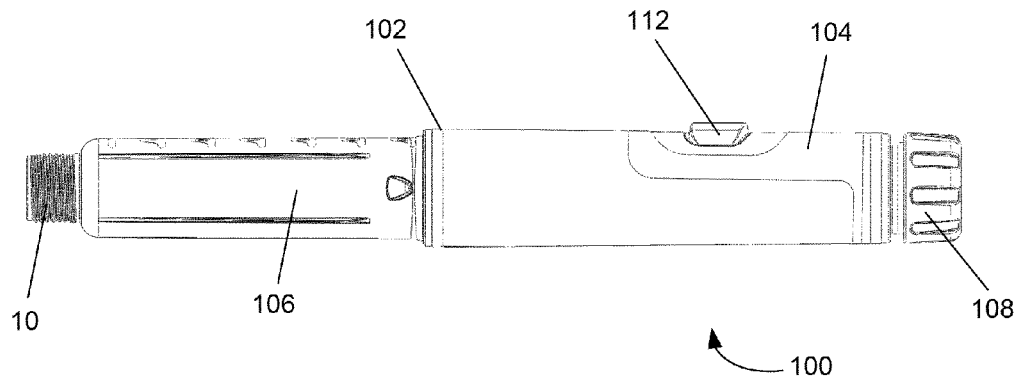
FIG. 1 shows an external view of a drug delivery device suitable for implementing the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together is such a way as the drug cartridge is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a button (not shown) which must be depressed in order to deliver the set drug dose. The display 112 may be configured to display information on the drug dose which has been set and/or delivered. The display 112 may further show additional information, such as the actual time, the time of the last usage/injection, a remaining battery capacity, one or more warning signs, and/or the like.

Figure 2:
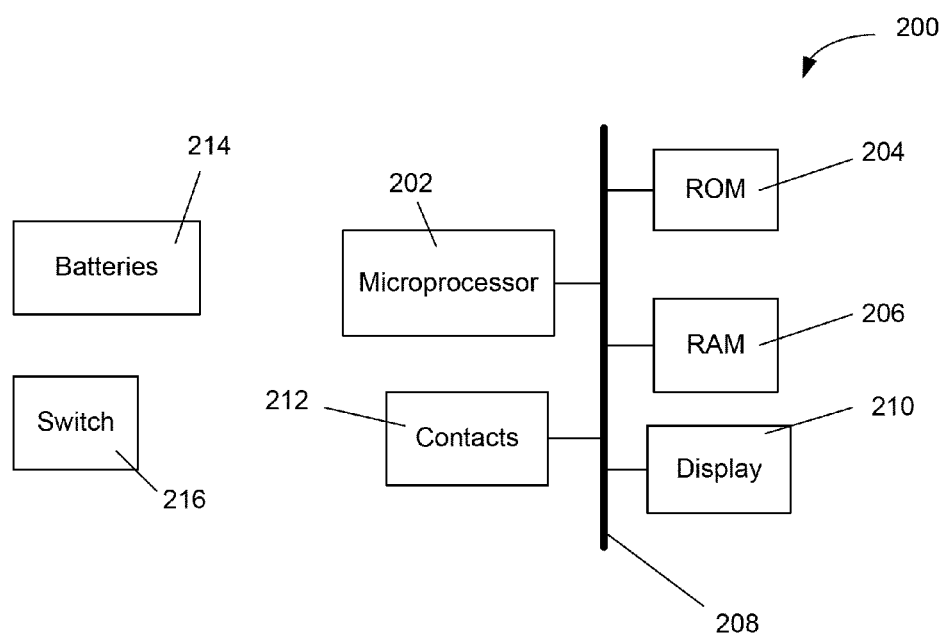
FIG. 2 shows a schematic diagram of some of the electronic components present in the drug delivery device of FIG. 1.

Referring now to FIG. 2, a schematic diagram of electrical circuitry 200 forming part of the drug delivery device 100 is shown. The circuitry 200 comprises a microprocessor 202, a non-volatile memory such as a ROM 204, a volatile memory such as a RAM 206, a display 210, contacts 212 and a bus 208 connecting each of these components. The circuitry 200 also comprises batteries 214 or some other suitable source of power for providing power to each of the components and a switch 216, described in greater detail below.

The circuitry 200 may be integral with the device 100. Alternatively, the circuitry 200 may be contained within an electronic module that can be attached to the device 100. In addition, the circuitry 200 may comprise additional sensors, such as optical or acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display 210. As such the microprocessor may also comprise a display driver.

The batteries 214 may provide power for each of the components including the contacts 212. The supply of electricity to the contacts 212 may be controlled by the microprocessor 202. The microprocessor 202 receives signals from the contacts 212 and so can determine when the contacts are energised, and is configured to interpret these signals. Information is provided on the display 210 at suitable times by operation of the software/firmware and the microprocessor 202. This information may include measurements determined from the signals received by the microprocessor 202 from the contacts 212.

A number of contacts 212 may be present in the device 100. In a preferred embodiment, seven contacts 212 are present and may be addressed individually by the microprocessor. These seven contacts 212 are arranged into two groups of contacts. In some embodiments, five contacts 212 comprise a first group of contacts and two contacts 212 comprise a second group of contacts. The contacts 212 may be mounted on an inner surface of the housing 102.

Figure 3:
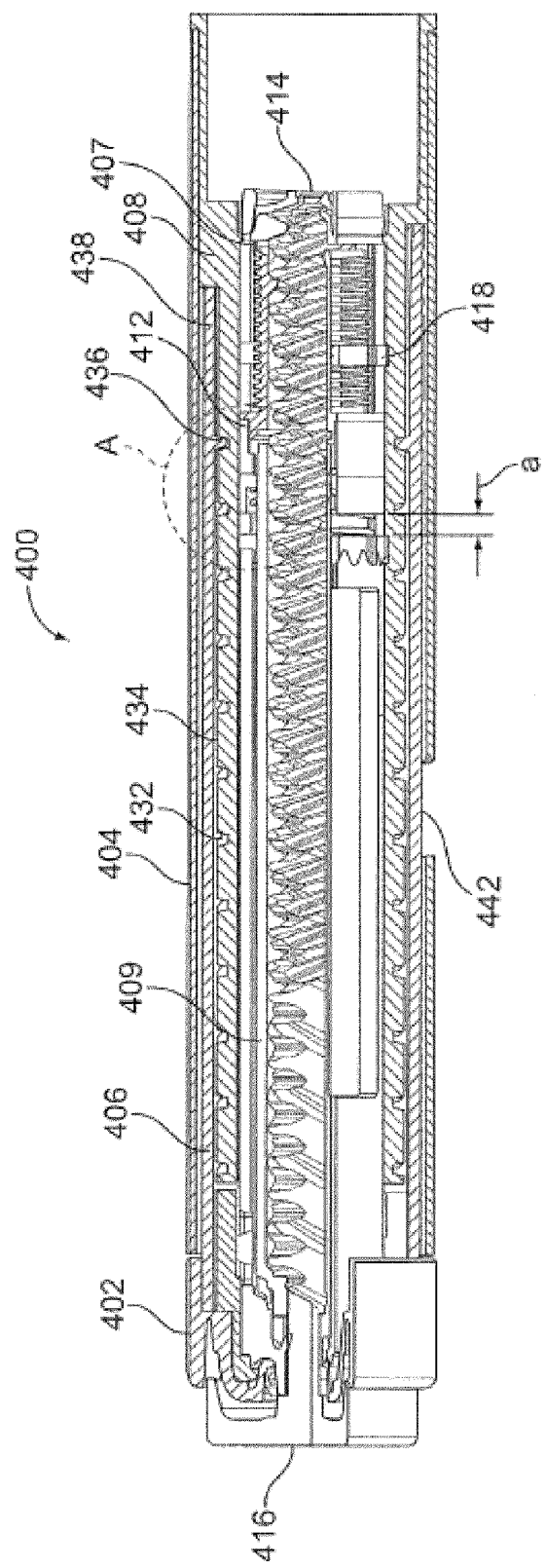
FIG. 3 shows a dose setting mechanism of a drug delivery device suitable for use with the invention.
Figure 4:
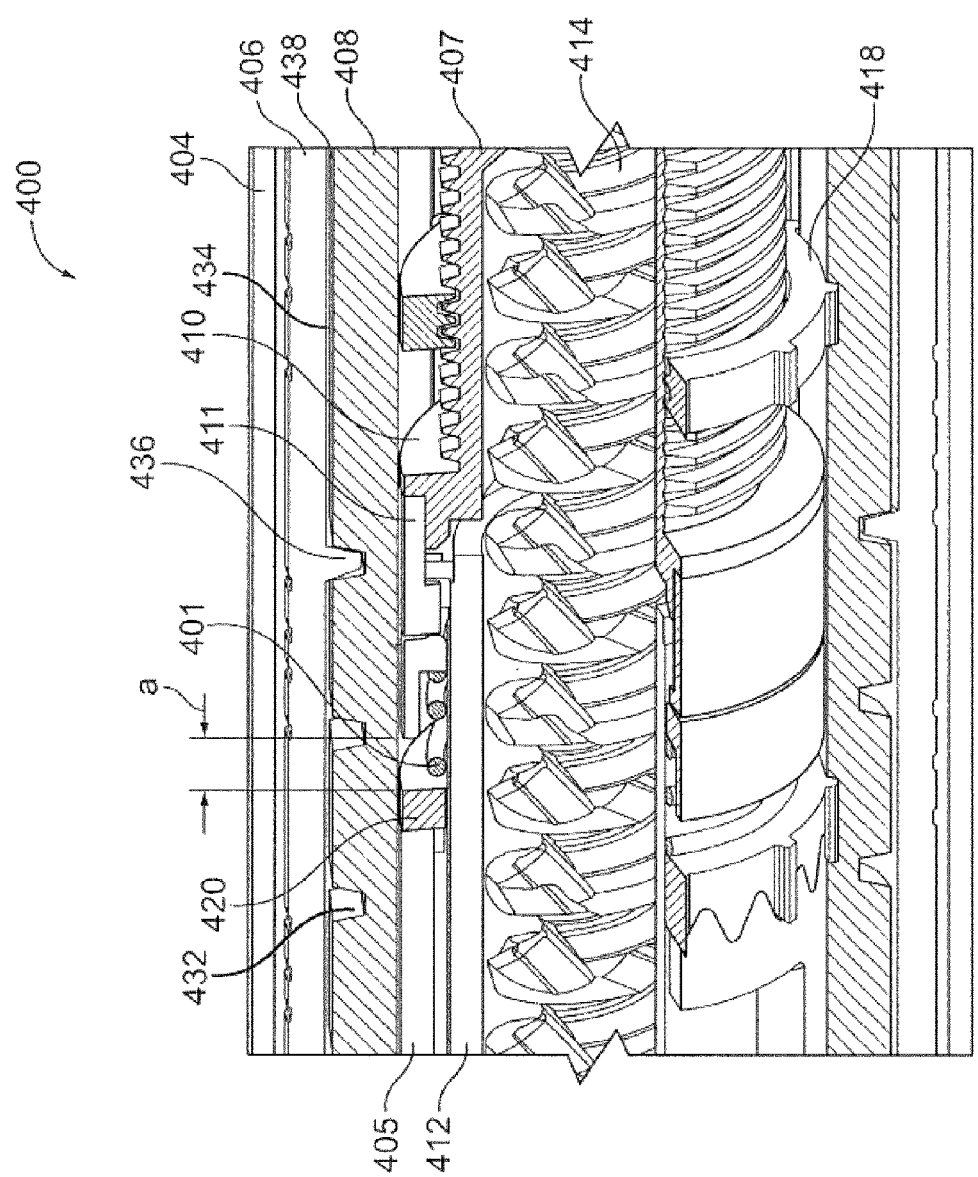
FIG. 4 shows detail of the dose setting mechanism of FIG. 3.
Figure 5:
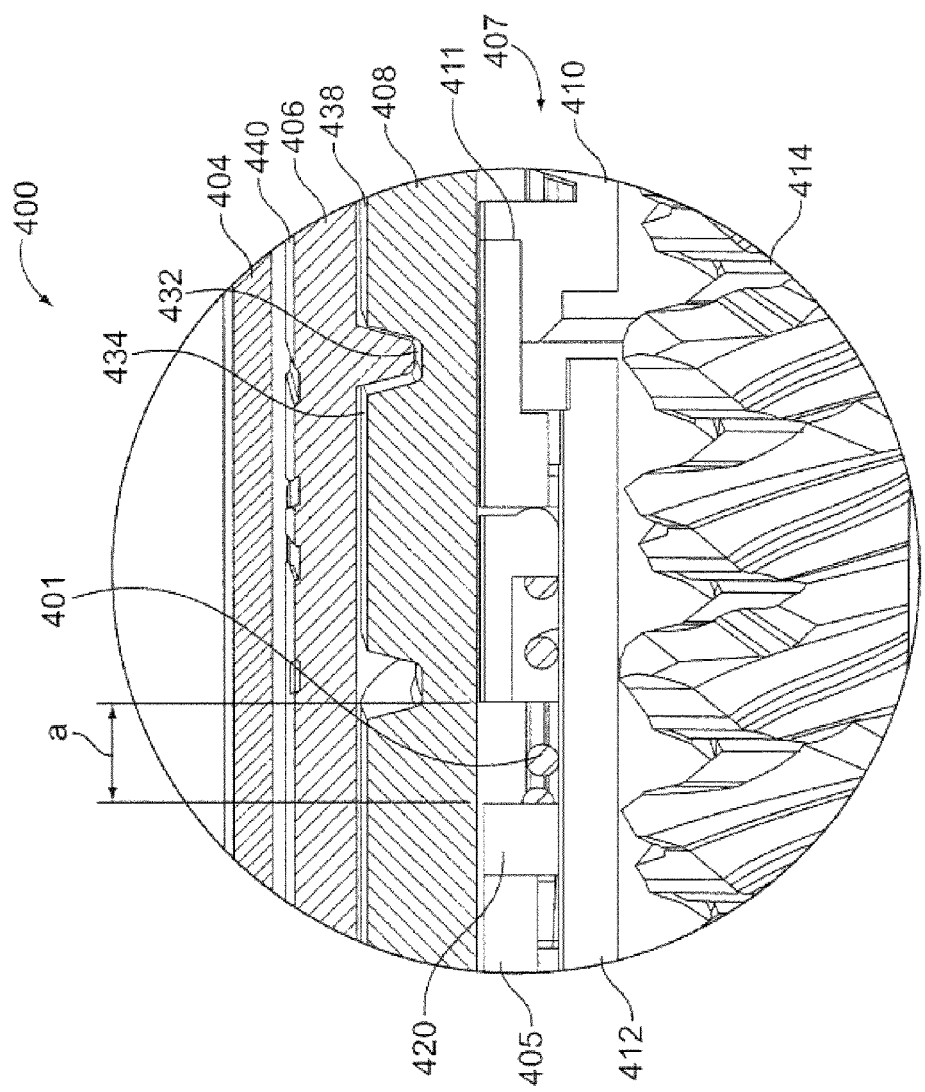
FIG. 5 shows a close up of the region marked 'A' in FIG. 3.

A fuller explanation of the operation of the dose setting and delivery mechanism supported within the second housing part 106 will now be given with reference to FIGS. 3 to 6. FIG. 3 is a cross-sectional view of a dose setting mechanism 400 of a drug delivery device. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and an encoded member 406. These components are preferably hollow cylinders arranged concentrically. The encoded member 406 is disposed between the outer and inner housings 404, 408. The inner housing 408 comprises a groove 432 provided along an external surface 434 of the inner housing 408. A groove guide 436 provided on an inner surface 438 of the encoded member 406 is rotatably engaged with this groove 432. The encoded member 406 has information encoded on its outer surface 440 as will be described in more detail below with reference to FIGS. 7 and 8.

A dose dial grip 402 is located at a proximal end of the outer housing 404. The dose dial grip 402 is disposed about an outer surface of a proximal end of the encoded member 406. An outer diameter of the dose dial grip 402 preferably corresponds to the outer diameter of the outer housing 404. The dose dial grip 402 is secured to the encoded member 406 to prevent relative movement between these two components. The dose dial grip 402 is represented in the external view of FIG. 1 by the rotatable dial 108. The dose dial grip 402 supports a dose button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle.

Each groove form is effectively continuous over a number of turns. In one preferred arrangement, each groove of the spindle 414 engages either a non-continuous helical groove form on a body portion or on a driver. Preferably, either or both a non-continuous thread form on a body and a driver consists of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. In one arrangement, the first driver portion 407 comprises a first component part 410 and a second component part 411. Alternatively, the first driver portion 407 is an integral component part.

With the dose setting mechanism 400, as a user dials a dose with the dose dial grip 402, the metal spring 401 is selected to be strong enough to maintain engagement of both clutched couplings: the clutched coupling between the clutch 405 and the encoded member 406 and clutched coupling between the first driver portion 407 and second driver portion 412. The encoded member 406 is coupled to the dose dial grip 402 such that when a user rotates the dose dial grip 402, the encoded member 406 also rotates. As the encoded member 406 is rotated in a first rotational direction, it moves axially in a proximal direction due to its threaded connection to the inner housing 408.

When the drug delivery device is being dispensed, the user applies an axial load to the dose button 416 located at the proximal end of the mechanism 400. The dose button 416 is axially coupled to the clutch 405 and this prevents relative axial movement. Therefore, the clutch 405 moves axially towards the cartridge end or the distal end of the dose setting mechanism 400. This movement disengages the clutch 405 from the encoded member 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
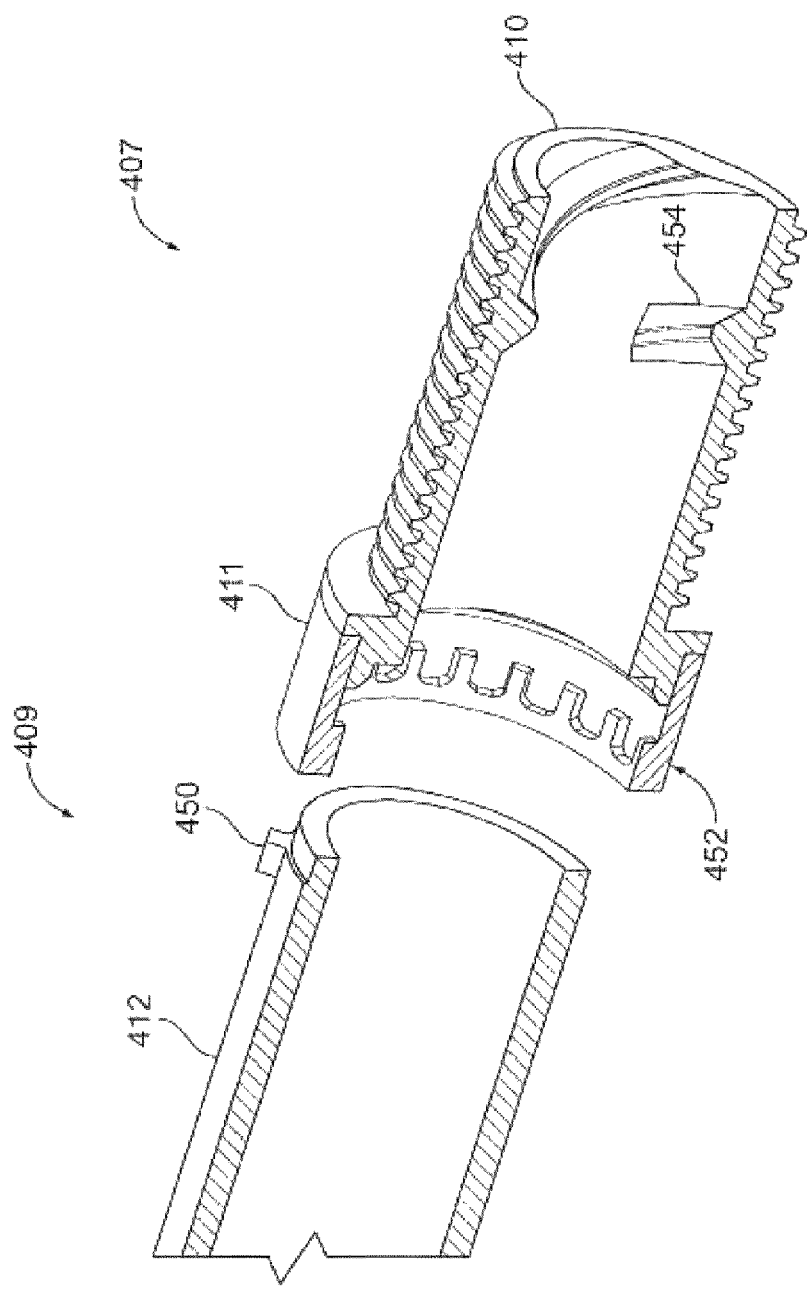
FIG. 6 is an exploded view showing details of a driver forming part of the dose setting mechanism of FIGS. 3 to 5.
Figure 10:
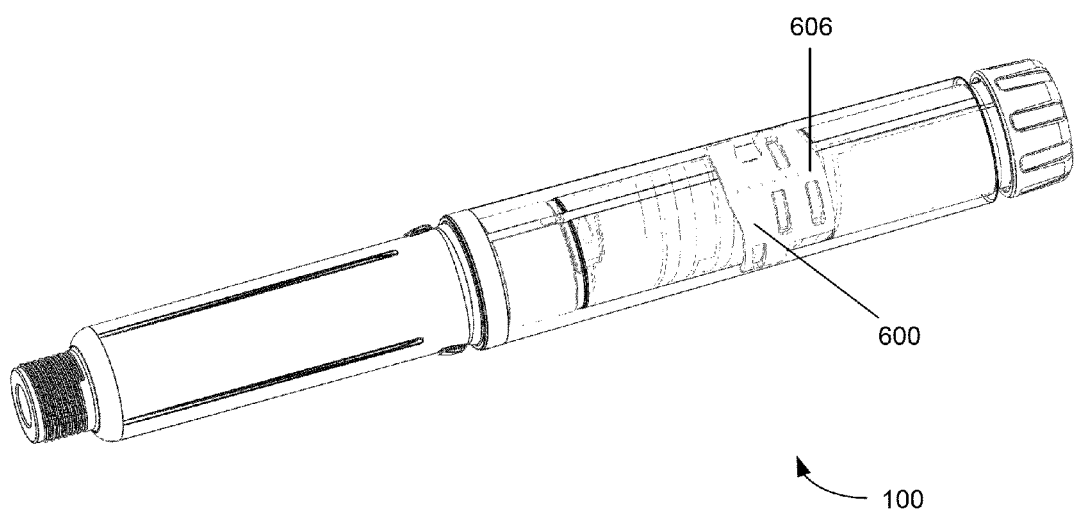
FIG. 10 shows the contact support member of FIG. 9 in position within the drug delivery device.

FIG. 6 shows in detail a first arrangement of the first driver portion 407 and the second driver portion 412 illustrated in FIGS. 3 to 5. As illustrated in FIG. 10, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove rather than a complete helical groove. One advantage of this arrangement is that it is generally easier to manufacture.

One advantage of this dose setting mechanism 400 utilizing the inner housing 408 is that the inner housing 408 can be made from an engineering plastic that minimizes friction relative to the encoded member 406 groove guide 436 and the groove 432. For example, one such an engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the encoded member 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the Microprocessor 202, ROM 204, RAM 206, display electronics and batteries 214 previously described. A number of the contacts 212 may be supported on a lowermost surface of the insert, while others of the contacts 212 may be supported at other positions on the inner surface of the outer housing 404 and linked to the microprocessor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the encoded member 406 in order to facilitate a determination of the rotational position of the encoded member 406, as will be described in more detail with reference to FIGS. 7 to 10.

The dose setting mechanism 400 illustrated in FIG. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is de-coupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually de-couple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the encoded member 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the encoded member 406. As a consequence, the encoded member 406 cannot rotate relative to the inner housing 404. If the encoded member 406 is prevented from rotating then, as the spindle 414 is retracted back into the dose setting mechanism 400 and thereby re-set, there will be no risk of the encoded member 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver portion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the encoded member 406 and for implementing the present invention. It will be apparent to the skilled person that other mechanisms may also be suitable. For example, a mechanism which does not include an inner housing 408, but in which the encoded member 406 is still visible to the sensor 112 would be equally suitable.

Figure 7:
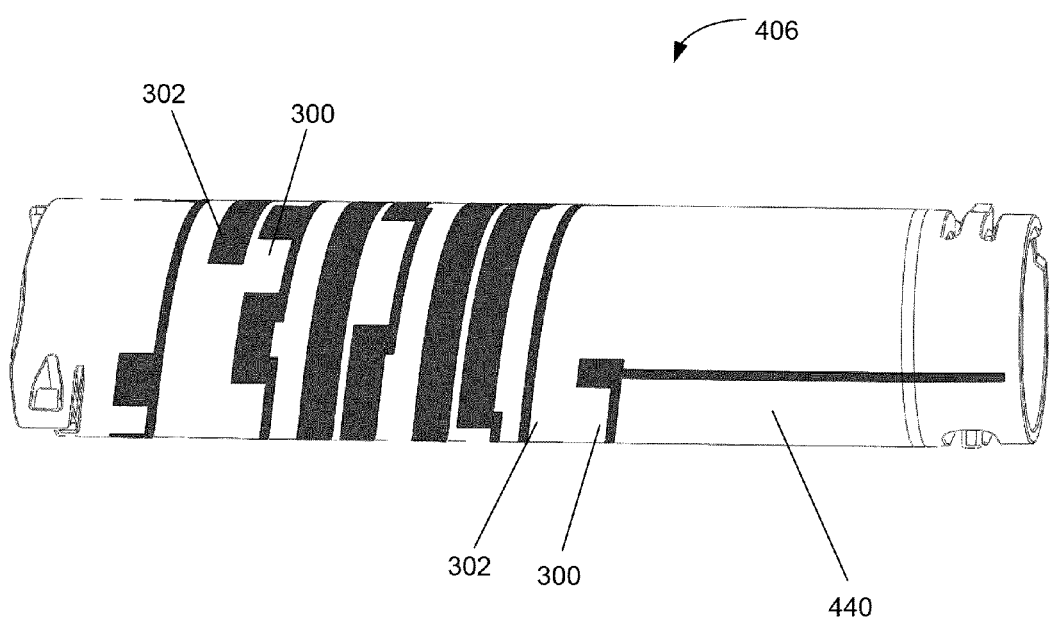
FIG. 7 shows an encoded member according to an embodiment of the invention.

FIG. 7 illustrates the encoded member 406. The encoded member 406 is a hollow cylinder. An outer surface 440 of the encoded member 406 comprises a first helical track 300 and a second helical track 302 arranged adjacent to one another. Each of the first and second tracks 300, 302 comprises conductive and non-conductive segments. In FIG. 7, the conductive segments are shown in black and the non-conductive segments are shown in white. In some embodiments, each of the first and second tracks 300, 302 comprises a measurement track and a ground or power track immediately adjacent to the measurement track. The effect of the ground track is to maintain an electrical connection between all of the conductive segments of each track 300, 302.

An inner surface 438 of the member 406 may have a helical thread (shown as inner groove 436 in FIGS. 3 to 5). This thread 436 may extend over a single turn or over a partial turn. Alternatively, this thread 436 may comprise several turns. The member 406 may be made of a plastic material. The encoded member 406 is configured to be incorporated into the drug delivery device 100 as shown in FIGS. 3 to 5. The inclusion of an inner housing 408 enables the encoded member 406 to have a helical thread 436 on the inner surface 438 rather then the outer surface 440. This results in a number of advantages. For example, this results in the advantage of providing more surface area along the outer surface 440 of the encoded member 406 for the helical tracks 300, 302. Another advantage is that this inner groove 436 is now protected from dirt ingress. In other words, it is more difficult for dirt to become logged in this inner groove interface than if the groove were provided along the outer surface 440 of the encoded member 406. This feature is particularly important for a re-settable drug delivery device which is required to function over a much longer period of time compared to a non-resettable device.

The helical tracks 300, 302 formed on the outer surface 440 of the member 406 may be formed by wrapping one or more metallic strips around the member 406. The metallic strip 300, 302 may have a non-conductive backing to support the metallic layer. The non-conductive backing may have an adhesive on the reverse side for securing the strip to the outer surface 440 of the member 406. The first and second helical tracks 300, 302 may be separated by a non-conductive strip. In some other embodiments, the tracks 300, 302 may comprise conductive ink printed onto a non-conductive substrate. This non-conductive substrate may be the member 406 itself or a secondary substrate which is subsequently attached to the member 406.

An electrical conduction path (not shown) joins the two tracks 300, 302. The switch 216 is disposed in this electrical conduction path. The switch 216 is configured to connect electrically the two tracks 300, 302 to one another when the device 100 is idle or when a drug dose is being set by rotation of the rotatable dial 108. The switch 216 is configured to isolate electrically, or disconnect, the two tracks 300, 302 when the selected drug dose is being delivered. The switch 216 is coupled to the dose button 416 supported by the rotatable dial 108, such that when the button is depressed, the switch 216 disconnects the two tracks 300, 302 from one another.

Each of the first and second tracks 300, 302 is configured to be engaged by a number of contacts 212. The contacts 212 may be biased against the outer surface 440 of the encoded member 406 in order to provide a stable electrical connection. The contacts 212 are spaced along the length of their respective track 300, 302. The contacts 212 are arranged to engage, if present, the measurement track of their respective helical track 300, 302. In a preferred embodiment, the first track 300 is engaged by five contacts 212 (contacts 1-5) and the second track 302 is engaged by two contacts 212 (contacts 6 and 7). The pitch of the helical tracks 300, 302 is the same as the pitch of the groove guide 436 of the encoded member 406 which engages with the inner housing groove 432. Therefore, when the encoded member 406 rotates and moves axially within the housing 102, the helical tracks 300, 302 are always positioned directly underneath the contacts 212. The contacts 212 are spaced such as to engage non-adjacent segments of their respective track 300, 302. In some embodiments, contacts 1 to 5 are spaced so as to engage every 6th segment of the first track 300 and contacts 6 and 7 are spaced so as to engage every 27th segment of the second track 302.

The microprocessor 202 may be configured to address each of the contacts 212 individually. The microprocessor 202 is also configured to control the flow of electricity from the batteries 214 to each contact. However, when the batteries 214 provide a signal having a voltage to one of the contacts, certain others of the contacts may also be energized by virtue of being in electrical connection with the first contact via the conductive segments of the helical tracks 300, 302 or via the electrical conduction path joining the two tracks 300, 302. Thus, the batteries may provide a voltage to a first of the contacts (for example) and the microprocessor 202 may detect signals from each of the contacts 212 which are energized by their electrical connection to the first contact. Since the microprocessor 202 can address the contacts 212 individually, it is able to apply a signal to different contacts in a sequence, each time monitoring signals from the other contacts 212.

The conductive and non-conductive segments of the helical tracks 300, 302 are arranged in a repeating sequence. As the contacts 212 are spaced along the tracks 300, 302, each contact sees a shifted version of the same sequence of code. Having seven contacts 212 results in a seven bit encoding system. Seven bits allows for a maximum of 2⁷=128 unique positions to be encoded. Thus the full 0-80 unit dial-able dose for an injection device can be absolutely encoded with redundant positions available.

It should be noted that the first and second tracks 300, 302 do not begin at the same relative angular position on the encoded member 406 in the embodiment shown in FIG. 7. The tracks 300, 302 are offset such that the second track 302 begins and ends first. The start of the first track 300 and the end of the second track 302 are visible in FIG. 7.

Figure 8:
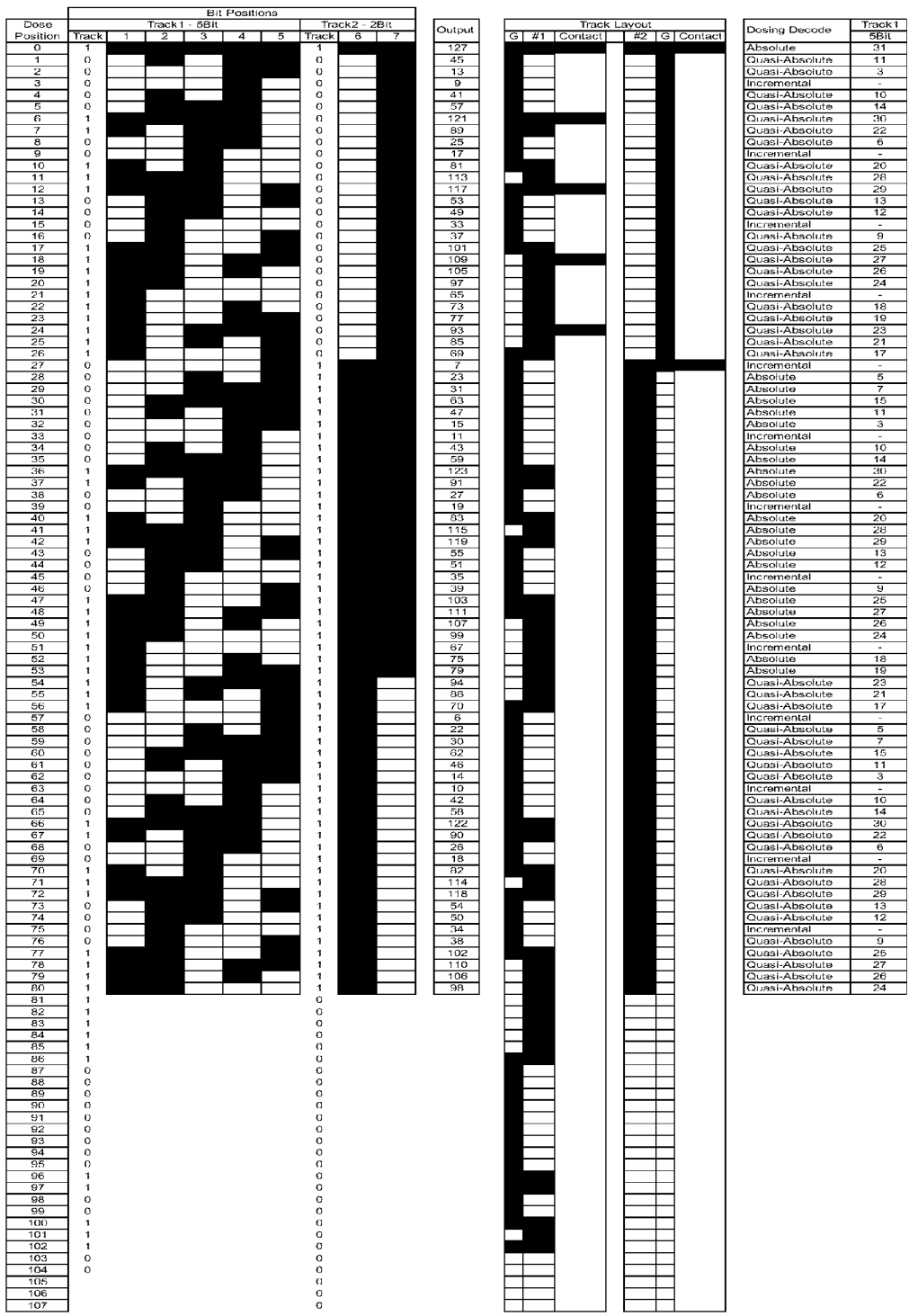
FIG. 8 is a table illustrating a track layout, contact positions, results as registered at the contacts and a dispensing mode decoding type.

FIG. 8 shows a table 500 illustrating a track layout for the first and second tracks 300, 302 and the track segments as registered at each of the seven contacts 212 in each rotational position. The arrangement of the segments of the first track 300 is shown in column "#1". The arrangement of the segments of the second track 302 is shown in column "#2". The columns headed "G" represent the ground or power tracks which are immediately adjacent to each of the measurement tracks (#1, #2). In FIG. 8, the darker regions represent a conductive segment and the lighter regions represent a non-conductive segment. A code digit with a value of "1" may be represented by a conductive segment and a value of "0" may be represented by a non-conductive segment.

The two columns headed "contact" illustrate the segment intervals between the contacts engaging the first and second tracks 300, 302 respectively in dose position "0". The columns headed 1 to 7 show the type of segment (conductive or non-conductive) positioned under each of the seven contacts 212 in each rotational position, represented by the column "Dose Position". The repeating sequence which is laid out on the first track 300 (column #1) is arranged such that when contacts 1 to 5 are positioned over every 6th segment (see first "contact" column), the result at these contacts forms a type of Gray code, or reflected binary code, as shown in columns 1-5 of the table 500. A Gray code is a binary coding system in which only one binary bit changes value between each successive encoded value. The illustrated Gray code repeats every 30 rotational positions. Coupled with the output from contacts 6 and 7, which changes every 27 rotational positions (see second "contact" column), the rotational position of the encoded member 406, and hence the dose position, can be determined absolutely.

Contacts 6 and 7 engage with the second track 302 at an interval of 27 segments. Thus the second track 302 is 27 segments longer than the 81 needed to encode the dose positions 0-80, i.e. when the sixth contact is positioned over the 81st segment, the seventh contact is positioned over the 108th segment. Similarly, the first five contacts are spaced at intervals of 6 segments meaning that the first track 300 is 24 segments longer than the 81 needed to encode the dose positions 0-80, i.e. when the first contact is positioned over the 81st segment, the fifth contact is positioned over the 105th segment.

The Gray code shown in columns 1 to 5 of the table 500 deviates from a pure Gray code such that at position zero contacts 1 to 5 all have a value of "1". This arrangement aids with error checking of the device 100 as any inoperable contacts will not initially register a value.

Each conductive segment within each track 300, 302 is electrically connected to every other conductive segment within that track due to the presence of the ground or power tracks. Thus, in all rotational positions of the encoded member 406, when a voltage is provided from the batteries 114, via a contact 212, to a conductive segment, every conductive segment on the respective track 300, 302 is also energized. Any contact 212 (other than the contact which has the voltage provided to it) which is positioned over a conductive segment therefore registers a binary value of "1".

Figure 9:
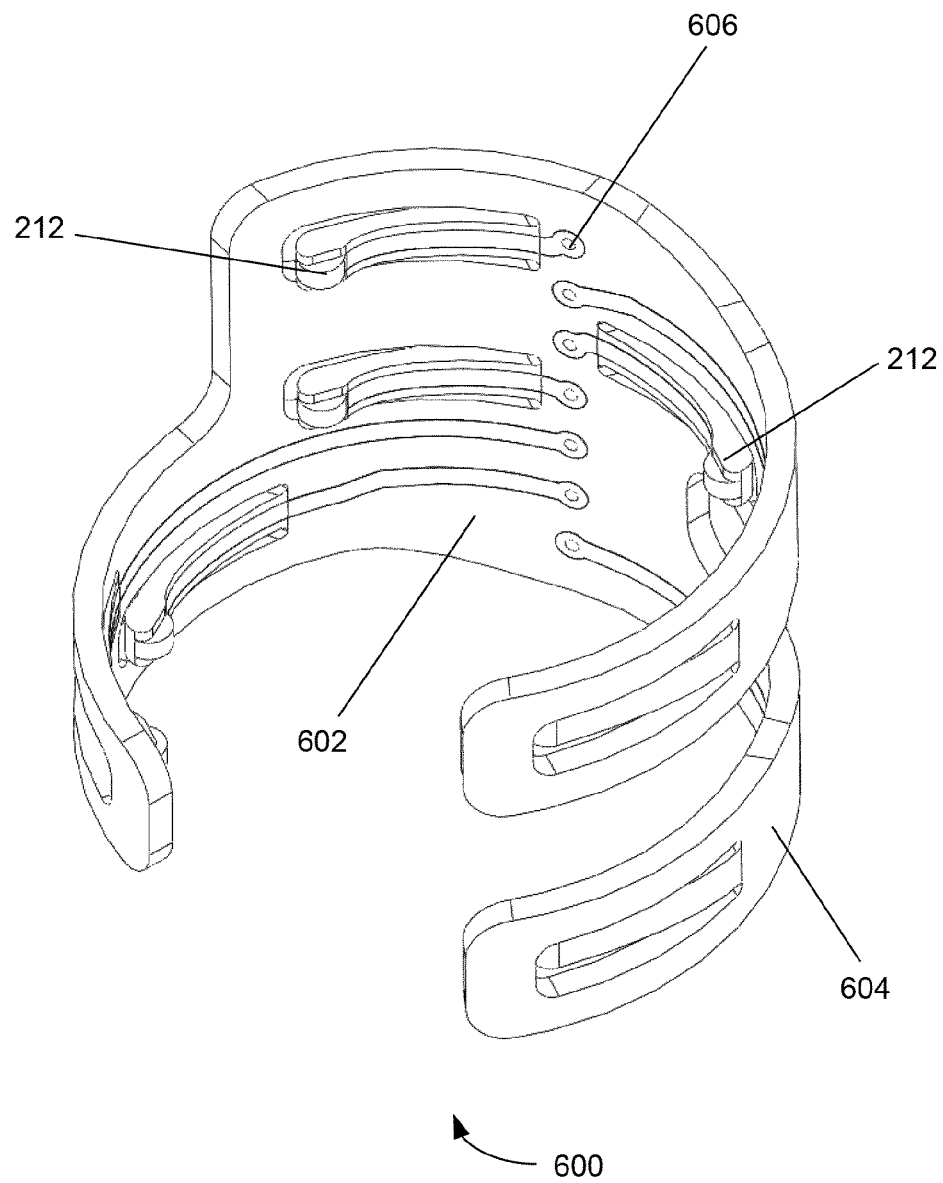
FIG. 9 shows a contact support member.

FIG. 9 shows a contact support member 600 supporting seven contacts 212. FIG. 10 shows the contact support member 600 in position within the drug delivery device 100. The contact support member 600 may have a generally cylindrical hollow body. The support member 600 may be a partial cylinder (as shown in FIG. 9), or it may be a full cylinder. The contacts 212 are supported on an inner surface 602 of the support member 600. The support member 600 is configured to extend about the encoded member 406 such that the contacts 212 engage with the tracks 300, 302 on the encoded member 406. An outer surface 604 of the support member 600 may abut directly an inner surface of the outer housing 404 and may be secured to the outer housing 404 in order to prevent relative movement between these components. Alternatively a recess (not shown) may be provided in the outer housing 404 to accommodate the contact support member 600.

Each contact 212 has a respective contact terminal 606. The contact terminals 606 may extend through the thickness of the contact support member 600 so that the contacts 212 may be addressed from the outer surface 604 of the support member 600. The contacts 212 may have a sprung bias towards the encoded member 406 such that a stable connection is made between each contact 212 and the tracks 300, 302. The contacts 212 are positioned such that contacts 1 to 5 engage the first track 300 at every 6th segment and contacts 6 and 7 engage the second track 302 at every 27th segment. The microprocessor 202 and other electronic components may be located adjacent to the contact terminals 606 on the outer surface 604 of the contact support member 600.

When a user of the device 100 rotates the rotatable dial 108 to set a drug dose, the microprocessor 202 may be activated and may be controlled by software stored in the ROM 204 to execute a predefined check on the contacts 212 to determine the absolute rotational position of the encoded member 406, and hence the drug dose which has been dialled. This checking process may also allow the microprocessor 202 to determine the status of the switch 216 and hence whether the device 100 is in dialling mode or dispensing mode. If the microprocessor 202 determines that the device 100 is in a dispensing mode, further steps may be preformed in order to determine the rotational position of the encoded member 406. The microprocessor 202 may also be configured to determine the number of drug units which have been delivered.

Figure 11:
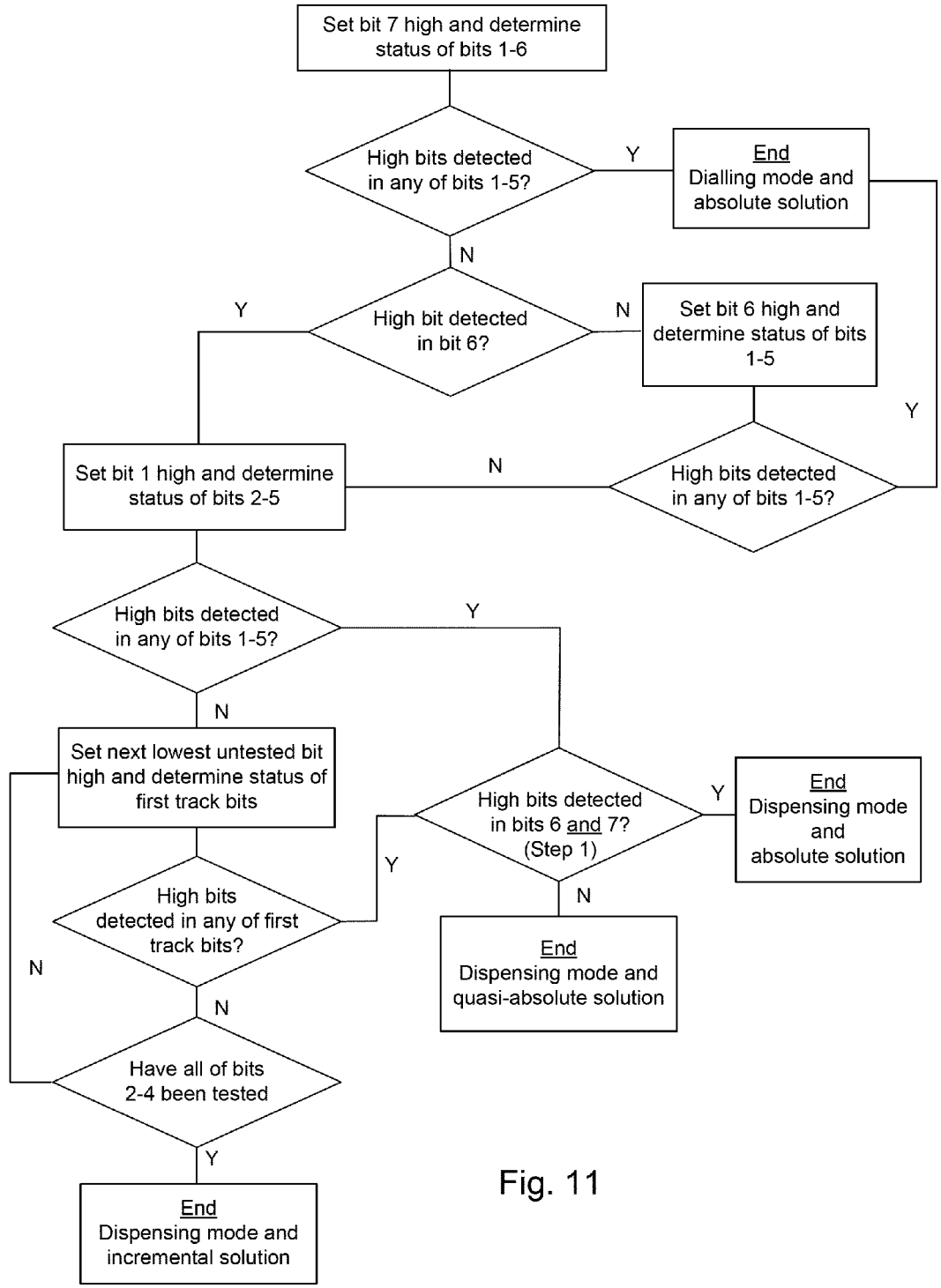
FIG. 11 is a flow chart illustrating the steps involved in determining the rotational position of the encoded member.

Referring to FIG. 11, the process of determining the rotational position of the encoded member 406 is now described. Each contact 212 represents a bit of the encoding system and may alternatively be referred to as "bits". When a contact 212 is positioned over a conductive segment, it may be referred to as a "high bit". When a contact 212 is positioned over a non-conductive segment, it may be referred to as a "low bit". A contact 212 or bit may be "set high" by applying a voltage to it in some way. Each of the contacts 212 may individually have a voltage applied and the status (high or low) of each bit may be individually determined by the microprocessor 202.

In step S1, bit 7 is set high by the microprocessor 202 and the status of bits 1 to 6 are determined. As previously mentioned, the microprocessor 202 may receive electrical signals from each of the contacts 212 and may be configured to interpret these signals to determine the binary code digit for the contacts 212.

At step S2 it is determined whether any of bits 1 to 5 were detected as "high" in step S1. If any high bits were detected in bits 1 to 5 then, at step S3, the microprocessor 202 can use the result of the bit determination in step S1 to conclude that the device 100 is in a dialling mode and to determine absolutely the rotational position of the encoded member 406 and hence the drug dose which has been dialled. The microprocessor 202 may achieve this by searching a lookup table stored in the ROM 204, the lookup table providing a conversion from a seven bit binary code result to a dose unit dialled. The process ends at step S3 while requiring only steps 1 and 2 to be performed in the situation where a user of the device 100 dials between 0 and 53 units.

If at step S2 none of bits 1 to 5 are determined to be "high", then the microprocessor 202 proceeds to step S4, in which it is determined if bit 6 was detected as high in step S1. If bit 6 was not detected as high then, at step S5, bit 6 is set high and the status of bits 1 to 5 are determined. At step S6 it is determined whether any of bits 1 to 5 were detected as "high" in step S5. If any high bits were detected in bits 1 to 5 then, at step S3, the microprocessor 202 can use the result of the bit determination in step S5 to conclude that the device 100 is in a dialling mode and to determine absolutely the rotational position of the encoded member 406 and hence the drug dose which has been dialled. Steps 1 to 6 of the process are performed before the process ends at step S3 in the situation where a user of the device 100 dials between 54 and 80 units.

If bit 6 is detected as high in step S4, or if bit 6 is not detected as high in step S4 but no high bits are subsequently detected in bits 1 to 5 in steps 5/6, then the process proceeds at step S7. The microprocessor 202 may also determine at this point in the process that the device 100 is in a dispensing mode. Because there is at least one conductive segment on each track 300, 302 at each rotational position, the fact that no high bits were detected in bits 1 to 5 at either step S2 or, if performed, step S6 means that the two tracks 300, 302 are not electrically connected. As previously described, this occurs when the dose button 416 is depressed causing the switch 216 to isolate electrically, or disconnect, the two tracks 300, 302. When the dose button 416 is depressed, the device is in a dispensing, or drug delivery, mode.

At step S7, bit 1 is set high by the microprocessor 202 and the status of bits 2 to 5 are determined. At step S8 it is determined whether any of bits 2 to 5 were detected as "high" in step S7. If any high bits were detected in bits 2 to 5 then, at step S9, it is determined whether both bit 6 and bit 7 were detected as "high" in step S1. If both bit 6 and bit 7 were detected as high in step S1 then, at step S10, the microprocessor 202 can use the results obtained in steps 1 and 8 to determine absolutely the rotational position of the encoded member 406. As previously mentioned, the microprocessor 202 may determine that the device is in a dispensing mode upon reaching step S7 of the process but may only record this determination upon reaching a process end step.

If both bits 6 and 7 are not detected as "high" in step S9, i.e. neither bit 6 or 7 is detected as high then, at step S11, the microprocessor 202 records that the device is in a dispensing mode and that a quasi-absolute solution may be determined. In the quasi-absolute solution scenario, the microprocessor 202 may search a five bit lookup table (or the first five bits of the seven bit lookup table) stored in the ROM 204. This search yields more than one possible position, and since neither bit 6 not bit 7 were detected as high, these positions yield the same bit code result. Due to the isolation of the second track 302 from the first, there is no situation in which only one of bit 6 or bit 7 is detected as high.

Referring back to FIG. 8, the last columns of the table 500 list the type of solution which can be determined for each rotational position when the device 100 is in a dispensing mode. Quasi-absolute solutions are present in both the first and last 27 dose positions. For example, dose positions 6 and 66 are indistinguishable from one another when the first and second tracks 300, 302 are not electrically connected together. However, the microprocessor 202 may still determine or predict the position of the encoded member 406 using the last known absolute position. For example, if a user dials a dose of 10 units and then delivers only 4 of those units, the microprocessor 202 can determine that the current rotational position is dose position 6, rather than position 66, since the last absolutely known position was much lower than position 66, and it is mechanically prevented for the dial position to increase whilst the device is in dispensing mode.

At step S8 it is determined whether any of bits 2 to 5 were detected as "high" in step S7. If no high bits were detected in bits 2 to 5 then, at step S12, the next lowest untested bit is set high and the status of the other first track bits are determined. For example, if the result of step S8 is negative, then bit 2 is set high in step S12 and the status of bits 1, 3, 4 and 5 are determined. At step S13 it is determined whether any high bits were detected in step S12. If it is determined that high bits were detected then the process continues to step S9, described above. If high bits are not detected in any of the first track bits at step S13 then, at step at 14, it is determined whether all of bits 2 to 4 have been tested. If all of bits 2 to 4 have not been tested then the process returns to step S12, where the next lowest untested bit is tested. For example, if bit 2 is set high in step S12 and it is determined in step S13 that no high bits are detected in any of the first track bits, then the result of step S14 will be negative and the process will return to step S12, in which bit 3 is set high and the status of bits 1, 2, 4 and 5 are determined.

If at step S14 it is determined that all of bits 2 to 4 have been tested then the process ends at step S15 where the microprocessor 202 records that the device is in a dispensing mode and that an incremental solution may be determined. In this situation the microprocessor 202 has not been able to establish the status of any of the seven bits. The microprocessor 202 therefore predicts the dose position based on the last know absolute position.

As can be seen from the table 500 of FIG. 8, during dispensing of the device 100 there are 23 dose positions which can be absolutely determined. There are 45 positions in which the 5 bit track 300 can be decoded to give a quasi-absolute solution. Repeated quasi-absolute solutions are separated by 60 dose positions. There are 13 positions, equally spaced every 6th dose, where an incremental solution must be determined.

In the depicted embodiment dose positions 58 to 60 have a quasi-absolute solution, however in some other embodiments, the software executed by the microprocessor 202 may allow these dose positions to be determined absolutely. For example dose positions 58 to 60 have the same five bit code, from bits 1 to 5 on track 300, as dose positions 28 to 30 respectively. No other dose positions return the same five bit codes. As dose positions 28 to 30 can be absolutely determined during dispensing as both bit 6 and bit 7 would be detected as "high" in step S1, dose positions 58 to 60 can be deduced absolutely as uniquely coded positions.

When dispensing a selected dose, if for any reason the user does not dispense the full dose, the display 210 may be configured to show the dose which is remaining to be dispensed. In this situation, the microprocessor 202 may determine the drug dose which has been dispensed by subtracting a remaining drug dose from the initially dialled drug dose.

Although a seven bit system has been described, the method is equally applicable for any number of contacts greater than three. The seven bit system is preferred as it allows the full 0-80 unit dose range to be absolutely encoded.

In some alternative embodiments of the invention, the encoded member 406 may comprise a metallic ring having protrusions round the circumference representing the conductive "1" value of the binary code. The recesses representing binary "0" can then be filled with a non-conductive material.

In an alternative embodiment of the invention the operation of the switch 216 is reversed. In this alternative embodiment, the switch 216 is configured to disconnect electrically the two banks of tracks 300 when the device 100 is idle or when a drug dose is being set by rotation of the rotatable dial 108. The switch 216 is configured to connect the two banks of tracks 300 when the selected drug dose is being delivered. The switch 216 is coupled to the dose button 416 supported by the rotatable dial 108, such that when the button is depressed, the switch 216 connects the two banks of tracks 300.

The microprocessor 202 may perform the cyclic check described above while the encoded member is rotating, i.e. while the device is being dispensed. Therefore the same method as described above may be used to determine a dispensed dose, rather than a dialled dose.

Having determined the drug dose which has been dispensed, the microprocessor 202 may store the result in the ROM 204. The display 210 may be controlled to display the result of the dispensed dose determination. The display 210 may display the result of the dispensed dose determination for a predetermined time, for example 60 seconds. Alternatively or in addition, the dispensed dose history may be retrieved electronically from the ROM 204 by a user of the device 100 or by a health care professional. During dialling of the device, the dialled dose may be indicated to the user in any conventional way, for example by use of numerals printed on the number sleeve. Alternatively or in addition, a more complex cyclic check may be performed on the contacts 212 in order to determine the absolute rotational position of the encoded member 406 during dialling. This may involve checking each of the seven contacts in turn. In some other embodiments, the dialled dose is not determined or indicated to the user.

It will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28 unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A drug delivery device comprising:
   a housing;
   a cylindrical member configured to be rotatably supported inside the housing, wherein the outer surface of the cylindrical member is provided with at least first and second tracks together forming an encoder, each track comprising conductive segments and non-conductive segments, and wherein the at least first and second tracks are separated by a non-conductive strip;
   at least first and second groups of contacts configured to engage the first and second tracks respectively at predetermined intervals along the length of the track;
   a switch configured:
      in a first position, to connect electrically the first and second tracks, and
      in a second position, to isolate electrically the first and second tracks; and
   a processor configured:
      to cause a first electrical signal to be applied to a first contact of the second group of contacts and simultaneously to monitor electrical signals at the first group of contacts, and
      if electrical signals are not detected at any of the first group of contacts, to cause a second electrical signal to be applied to a second contact of the second group of contacts and simultaneously to monitor electrical signals at the first group of contacts.

2. The drug delivery device of claim 1, wherein the tracks are helical tracks and wherein the housing and the cylindrical member are configured such that the cylindrical member moves in a first axial direction relative to the housing when rotated in a first rotational direction relative to the housing.

3. The drug delivery device of claim 1, wherein the cylindrical member is configured to be rotatable from an initial position into a number of discrete rotational positions, and wherein the contacts of the first group of contacts are arranged such that the sequence of conductive and non-conductive segments engaged by the contacts of the first group of contacts in successive discrete rotational positions forms a Gray code.

4. The drug delivery device of claim 1, wherein the encoder has a higher bit depth than each individual track.

5. The drug delivery device of claim 1, wherein coding depths of the at least two tracks are combined such that a combined coding depth of the encoder comprising the at least first and second track equals the sum of the individual coding depth of each track.

6. The drug delivery device of claim 1, wherein each of the at least two tracks comprises a single track bit code.

7. The drug delivery device of claim 1, wherein the first group of contacts comprises more contacts than the second group of contacts.

8. The drug delivery device of claim 7, wherein the first group of contacts comprises five contacts and the second group of contacts comprises two contacts.

9. The drug delivery device of claim 1, wherein the contacts of the first group of contacts are spaced such as to engage every sixth segment of the first track and wherein the contacts of the second group of contacts are spaced such as to engage every twenty-seventh segment of the second track.

10. The drug delivery device of claim 1, further comprising a user actuatable plunger configured to cause expulsion of a drug from the drug delivery device, and wherein depression of the plunger causes the switch to switch from the first position to the second position.

11. The drug delivery device of claim 1, wherein the conductive segments within each of the first and second tracks are electrically connected to all of the other conductive segments in that track.

12. The drug delivery device of claim 11, wherein the conductive segments within each of the first and second tracks are electrically connected together by first and second common ground tracks immediately adjacent to respective ones of the first and second tracks.

13. The drug delivery device of claim 1, wherein the conductive and non-conductive segments of the first and second tracks are arranged such that, when the cylindrical member is in an initial position, each contact is configured to engage a conductive segment.

14. The drug delivery device of claim 1, wherein the device further comprises:
   a display, and
   wherein the processor is further configured to control the operation of the display.

15. The drug delivery device of claim 1, wherein the processor is further configured to: responsive to detecting no signals at any of the first group of contacts when the second electrical signal is applied to the second contact of the second group of contacts, cause a third electrical signal to be applied to a first contact of the first group of contacts and simultaneously to monitor electrical signals at the other contacts of the first group of contacts.

* * * * *